United States Patent
Watanabe et al.

(10) Patent No.: US 11,701,307 B2
(45) Date of Patent: Jul. 18, 2023

(54) ORGANIC-INORGANIC COMPOSITE PARTICLES, MANUFACTURING METHOD THEREFOR, AND COSMETIC

(71) Applicant: JGC CATALYSTS AND CHEMICALS LTD., Kawasaki (JP)

(72) Inventors: Satoshi Watanabe, Kitakyushu (JP); Naoyuki Enomoto, Kitakyushu (JP); Ikuko Shimazaki, Kitakyushu (JP)

(73) Assignee: JGC CATALYSTS AND CHEMICALS LTD., Kanagawa (JP)

( * ) Notice: Subject to any disclaimer, the term of this patent is extended or adjusted under 35 U.S.C. 154(b) by 104 days.

(21) Appl. No.: 16/979,341

(22) PCT Filed: Mar. 28, 2019

(86) PCT No.: PCT/JP2019/013871
§ 371 (c)(1),
(2) Date: Sep. 9, 2020

(87) PCT Pub. No.: WO2019/189692
PCT Pub. Date: Oct. 3, 2019

(65) Prior Publication Data
US 2021/0000705 A1      Jan. 7, 2021

(30) Foreign Application Priority Data
Mar. 30, 2018   (JP) ................. 2018-066583

(51) Int. Cl.
| | | |
|---|---|---|
| A61K 8/02 | (2006.01) | |
| A61K 8/25 | (2006.01) | |
| A61K 8/73 | (2006.01) | |
| A61Q 1/00 | (2006.01) | |
| C08J 3/16 | (2006.01) | |
| C08K 7/18 | (2006.01) | |
| C08K 7/26 | (2006.01) | |

(52) U.S. Cl.
CPC ........... *A61K 8/0279* (2013.01); *A61K 8/025* (2013.01); *A61K 8/25* (2013.01); *A61K 8/731* (2013.01); *A61Q 1/00* (2013.01); *C08J 3/16* (2013.01); *C08K 7/18* (2013.01); *C08K 7/26* (2013.01); *C08J 2301/02* (2013.01)

(58) Field of Classification Search
CPC .................................................. A61K 8/0279
See application file for complete search history.

(56) References Cited

U.S. PATENT DOCUMENTS

| | | |
|---|---|---|
| 9,011,888 B2 | 4/2015 | Nagata et al. |
| 10,314,769 B2* | 6/2019 | Watanabe ............. A61K 8/25 |
| 2005/0147908 A1 | 7/2005 | Yamane et al. |
| 2011/0287105 A1 | 11/2011 | Gittleman |
| 2012/0128748 A1 | 5/2012 | Nagata et al. |
| 2015/0157539 A1 | 6/2015 | Shimizu et al. |
| 2018/0280256 A1 | 10/2018 | Watanabe et al. |

FOREIGN PATENT DOCUMENTS

| | | | |
|---|---|---|---|
| CN | 104363879 A | | 2/2015 |
| EP | 1099544 A2 | | 5/2001 |
| EP | 2 462 915 A1 | | 6/2012 |
| JP | H07-196312 A | | 8/1995 |
| JP | 2002-265257 A | | 9/2002 |
| JP | 2003-012460 A | | 1/2003 |
| JP | 2005-128128 A | | 5/2005 |
| JP | 2008-273780 A | | 11/2008 |
| JP | 2013-527204 A | | 6/2013 |
| JP | 2013-136732 A | | 7/2013 |
| JP | 2014-043566 A | | 3/2014 |
| JP | 2016-002739 A | | 1/2016 |
| JP | 2017-186187 A | | 10/2017 |
| JP | 2018-172578 A | | 11/2018 |
| KR | 1020180079673 A | * | 7/2018 |

OTHER PUBLICATIONS

Cosmetics, Bao Yushan, China Textile Publishing Co., Ltd., Dec. 31, 1998.
Chinese Office Action dated Dec. 24, 2021 for the corresponding Chinese Patent Application No. 201980016948.7.
International Search Report issued in Patent Application No. PCT/JP2019/013871 dated Jul. 2, 2019.
Xue, J.M, et al: "PLGA/mesoporous silica hybrid structure for controlled drug release", Journal of Controlled Release (2004), pp. 209-217.

* cited by examiner

*Primary Examiner* — Gina C Justice
(74) *Attorney, Agent, or Firm* — Pearne & Gordon LLP

(57) ABSTRACT

There is provided a spherical organic-inorganic composite particle having good biodegradability. The organic-inorganic composite particle according to the present invention includes 1 to 79% by weight of a silica component and 21 to 99% by weight of a biodegradable plastic. The organic-inorganic composite particle has an average particle diameter $d_1$ of 0.5 to 25 μm, a true density of 1.03 to 2.00 g/cm$^3$, and a sphericity of 0.80 or more. A cosmetic product including the organic-inorganic composite particle having such properties has excellent texture properties.

10 Claims, No Drawings

ORGANIC-INORGANIC COMPOSITE PARTICLES, MANUFACTURING METHOD THEREFOR, AND COSMETIC

TECHNICAL FIELD

The present invention relates to spherical organic-inorganic composite particles having a suitable biodegradability, and a cosmetic product including the organic-inorganic composite particles

BACKGROUND ART

Today, synthetic polymers (plastics) derived from petroleum are being used in various industries, and support the convenience in our lives. Many of the synthetic polymers have been developed to secure long-term stability. Therefore, synthetic polymers are not degraded in natural environment, causing various environmental problems. One of such problems is that plastic products flowing out to aqueous environment accumulate for an extended period, and have significantly harmful effects on the ecosystems of oceans and lakes. Also, fine plastics having a length of from not more than 5 mm to nano levels, which are called micro-plastics, are recently considered as another serious problem. Examples of the micro-plastics include fine particles contained in cosmetic products and the like, small chunks of unprocessed plastic resin, and micro-pieces resulting from the fragmentation of large products floating in the sea.

Recent facial cleaners include plastic particles (e.g., polyethylene particles) having a size in orders of several hundreds of micrometers, so that the facial cleaners feel coarse and have an increased cleaning effect. Plastic particles, which have a small true specific gravity, are difficult to remove at sewage treatment plants, resulting in outflow into rivers, oceans, ponds, and the like. Since plastic particles are likely to adsorb chemicals such as pesticides, human bodies possibly have adverse effects due to biological concentration. This issue is also pointed out in the United Nations Environment Programme and the like. Various countries and industry associations are considering framing regulations against this problem.

Under such circumstances, biodegradable plastics are developed intensively and worldwide. The biodegradable plastics are decomposed into water and carbon dioxide by, for example, microorganisms in a natural environment. So, the biodegradable plastics are incorporated in a natural carbon cycle, for example, it is known that a cleaning agent including biodegradable plastic fiber-like particles having a particle diameter of 425 μm or more (see, for example, JP-A-2013-136732). It is also known a polylactic acid having an average particle size ranging from 1 μm to 44 μm is suitable for use in a cosmetic composition (see, for example, JP-A-2013-527204). Furthermore it is known a polylactic acid-based resin microparticles having a number average particle diameter less than 1 μm as biodegradable microparticles (see, for example, JP-A-2014-43566).

CITATION LIST

Patent Literature

Patent Literature 1: JP-A-2013-136732
Patent Literature 2: JP-T-2013-527204
Patent Literature 3: JP-A-2014-43566

SUMMARY OF INVENTION

Problems to be Solved by Invention

The biodegradable plastic particles of the prior art need a long time to naturally decompose if the plastic particles have a large particle size. The finer particles sizes are, the shorter the time necessary for natural decomposition becomes. However, microparticles firmly adhere to each other, and have a low flowability. If such microparticles are blended, as a texture improver, in a cosmetic product, the particles exhibit a strong adhesiveness. Thus, the microparticles of the prior art are not suitable as a texture improver which is required to have an appropriate spreadability. Further, biodegradable polymers of the prior art, which float on water and tend to absorb hazardous chemical substances and concentrate, cause environmental problems.

In view of the foregoing problems, it is an object of the present invention to provide organic-inorganic composite particles which have a suitable biodegradability, high sphericity and a mean particle diameter of 0.5 to 25 μm. The organic-inorganic composite particles having these characteristics are less likely to cause environmental problems and have a suitable flowability. Such organic-inorganic composite particles can be blended as a texture improver in a cosmetic product. Thus, the organic-inorganic composite particles can be put, with security, to the same uses as those for plastic beads.

Solution to Problems

The organic-inorganic composite particle according to the present invention is a spherical particle that includes 1.0 to 83.0% by weight of a silica component and 17.0 to 99.0% by weight of a biodegradable plastic. The average particle diameter $d_1$ is 0.5 to 25 μm, the true density is 1.03 to 2.00 $g/cm^3$, and the sphericity is 0.80 or more.

Furthermore, the contact angle to water of the organic-inorganic composite particle is 900 or less. Furthermore, the modulus of elasticity of the organic-inorganic composite particle is 2 to 30 GPa. Furthermore, when a dispersion liquid of the organic-inorganic composite particle is dispersed by an ultrasonic disperser for 60 minutes, a ratio $(d_3/d_1)$ between an average particle diameter $d_3$ after dispersion and an average particle diameter $d_1$ before dispersion is in the range of 0.95 to 1.05.

Also, the production method of the organic-inorganic composite particle according to the present invention includes an emulsification step of adding a surfactant and a nonaqueous solvent to a dispersion liquid containing a silica component and a biodegradable plastic thereby to prepare an emulsified liquid containing an emulsified droplet, a dehydration step of dehydrating the emulsified droplet, and a step of separating solid and liquid of the nonaqueous solvent dispersion body obtained in the dehydration step thereby to extract an organic-inorganic composite particle as a solid matter.

A cosmetic product of the present invention includes the organic-inorganic composite particles of any one of the foregoing aspects.

Effects of Invention

The organic-inorganic composite particles of the present invention do not float on water and have a reduced tendency to absorb hazardous water-insoluble chemical substances. In addition, the organic-inorganic composite particles have a suitable biodegradability. Thus, the organic-inorganic composite particles are less likely to cause environmental problems.

DESCRIPTION OF EMBODIMENTS

The organic-inorganic composite particle according to the present invention includes 1.0 to 83.0% by weight of a silica component and 17.0 to 99.0% by weight of a biodegradable plastic. Also, the average particle diameter $d_1$ is 0.5 to 25 µm, the true density is 1.03 to 2.00 g/cm$^3$, and the sphericity is 0.80 or more.

When the silica component is less than 1%, the effect as a binder provided by the silica component decreases, and the number of contact points between fine biodegradable plastics increase. Therefore, re-separation becomes difficult. On the other hand, when the biodegradable plastic is less than 17%, a soft sense and a moisture sense peculiar to plastic beads cannot be obtained. Furthermore, it is preferable that the silica component is 1 to 79% by weight, and the biodegradable plastic is 21 to 99% by weight. Particularly preferably, the silica component is 5 to 70% by weight, and the biodegradable plastic is 30 to 95% by weight.

If the organic-inorganic composite particles had a true density smaller than 1.03 g/cm$^3$, the organic-inorganic composite particles would float on water in a water environment, which would reduce a biodegradation rate. If the organic-inorganic composite particles had an absolute specific gravity greater than 2.00 g/cm$^3$, a content of the biodegradable plastic would decrease, and consequently, it would become difficult to obtain desired texture characteristics similar to those of plastic particles. It is particularly preferable that the organic-inorganic composite particles have a true density ranging from 1.10 g/cm$^3$ to 1.90 g/cm$^3$.

When the sphericity of the organic-inorganic composite particle is less than 0.80, the persistence of a rolling sense when the particle is applied on the skin significantly decreases. The sphericity is particularly preferably 0.90 or more. It is noted that the sphericity is calculated from a scanning electron microscopic photograph by an image analysis method.

When the average particle diameter $d_1$ of the organic-inorganic composite particle is less than 0.5 µm, texture properties of cosmetic products, such as a rolling sense, persistence of a rolling sense, and uniform spreadability, significantly decrease. On the other hand, when exceeds 25 µm, roughness is sensed when the particle powder is touched, and a soft sense and a moisture sense decrease. Also, the average particle diameter is more preferably 2 to 10 µm. It is noted that the average particle diameter is calculated by a laser diffraction method.

Furthermore, it is preferable that have a contact angle with water of the organic-inorganic composite particles is 90° or less. Organic-inorganic composite particle having a contact angle with water greater than 90° tends to float on water in a water environment, which may reduce a biodegradation rate. The contact angle depends on the properties of the biodegradable plastic that is a constituent component of the organic-inorganic composite particles. If the biodegradable plastic is hydrophobic, the organic-inorganic composite particles generally have a contact angle greater than 90°. In such a case, addition of a surfactant or other agents to the organic-inorganic composite particles can reduce the contact angle to 90° or less. Hydrophilic organic-inorganic composite particles having a contact angle of 90° or less have a reduced tendency to lower a biodegradation rate, and a reduced tendency to absorb water-insoluble hazardous chemical substances such as polychlorinated biphenyl compounds and insecticides. The contact angle with water of the organic-inorganic composite particles of the present invention is preferably smaller than 80°, and more preferably 70° or less.

It is preferable that the organic-inorganic composite particles have a modulus of elasticity within the range from 2 GPa to 30 GPa. A modulus of elasticity smaller than 2 GPa may result in a decrease in the strength of compressed product such as a powder foundation. This may lead to limitation of an amount of the organic-inorganic composite particles to be blended. A modulus of elasticity greater than 30 GPa makes the organic-inorganic composite particles less deformable in response to stress, and less soft and moist than plastic beads. It is particularly preferable that the modulus of elasticity be within the range from 3 GPa to 20 GPa. The modulus of elasticity can be determined by a micro compression test.

If the organic-inorganic composite particles are used in a cosmetic product, the particles may collapse during the manufacturing process of the cosmetic product, and the resultant cosmetic product may not have a function as initially expected. To address this problem, it is preferable that the mean particle diameter of the particles exhibit a rate of change remaining substantially the same before and after application of ultrasound to a dispersion liquid of the particles. Specifically, the organic-inorganic composite particles are dispersed in distilled water to obtain dispersion liquid. The dispersion liquid is to an ultrasonic disperser to be dispersed for 60 minutes. The ratio (d3/d1) between the mean particle diameter (d3) after the dispersion test and the mean particle diameter (d1) before the dispersion test is preferably within the range of 0.05, that is, between 0.95 and 1.05. The ratio (d3/d1) smaller than 0.95 means that the particles have a low strength and may collapse due to a mechanical load applied in the manufacturing process of a cosmetic product or other similar products, and that desired texture improvement may not be achieved. The ratio (d3/d1) greater than 1.05 means that the biodegradable plastic in particles easy to swell in water. As a result, the viscosity of the manufactured cosmetic product and other products tends to increase, making it impossible to ensure quality stability. This may also change the texture characteristics. It is particularly preferable that the ratio (d3/d1) is between 0.97 and 1.03.

Also, as the organic-inorganic composite particle, a particle having a hollow structure in which a cavity is formed inside a shell can be adopted. The hollow particle is lighter than a solid particle having an identical diameter. Therefore, when the component amount (% by weight) is identical, the number of hollow particles is larger than the number of solid particles.

It is noted that a ratio (T/OD) between a thickness T of the shell and an outer diameter OD of the organic-inorganic composite particle is preferably in the range of 0.02 to 0.45. When the shell thickness ratio (T/OD) exceeds 0.45, the particle comes to be substantially equivalent to a particle that does not have a hollow structure. On the other hand, when the shell thickness ratio is less than 0.02, the particle comes to easily break. Furthermore, the shell thickness ratio (T/OD) is particularly preferably in the range of 0.04 to 0.30. Here, the shell may be porous to allow nitrogen gas to pass through or may be nonporous to inhibit nitrogen gas from passing through.

The organic-inorganic composite particles preferably have a specific surface area per unit volume, determined by the BET method, ranging from equal to or greater than 5 m²/cm³ to smaller than 60 m²/cm³. The organic-inorganic composite particles having a specific surface area smaller than 5 m²/cm³ may have a reduced biodegradability. The organic-inorganic composite particles having a specific surface area of 60 m²/cm³ or more are categorized as a nanomaterial, and may become difficult to put to the same uses as those for the known plastic beads. It is particularly preferable that the specific surface area be equal to or greater than 10 m²/cm³ and smaller than 60 m²/cm.

A silica component and a biodegradable plastic included in the organic-inorganic composite particles of the present invention will be described in detail below.

<Silica Component>

Examples of the silica component contained in the organic-inorganic composite particles include a silicate binder and silica particles. For example, the silicate binder can be prepared through dealkalization of (e.g., removal of Na ions from) a silicate aqueous solution of an alkali metal silicate or an organic base silicate using a cation-exchange resin. Examples of the silicate include alkali metal silicates such as sodium silicate (water glass) and potassium silicate, and organic base silicates such as quaternary ammonium silicate.

A silica particle as used herein means an inorganic oxide particle containing silica, and examples thereof include complex oxides such as a silica-alumina complex oxide, a silica-zirconia complex oxide, and silica-titania complex oxide, and silica. The manufacturing conditions of the organic-inorganic composite particles do not need to be changed depending on difference in the composition of the silica particles. Taking into account inclusion of the organic-inorganic composite particles in a cosmetic product, amorphous silica is suitably used as the silica particles.

It is preferable that the silica particles have a mean particle diameter (d2) ranging from 5 nm to 1 μm. The mean particle diameter is particularly preferably within the range from 10 nm to 0.5 μm. If the mean particle diameter were greater than 1 μm, a binder effect of the biodegradable particles would decrease and the dissolution rate of silica in water environment would decrease, resulting in undesired deterioration of the suitable biodegradability. If the mean particle diameter were less than 5 nm, the stability of the silica particles would decrease. Such a decrease in the stability is industrially undesirable.

Further, the organic-inorganic composite particles may include, instead of the silica particles, inorganic oxide particles including at least one of titanium oxide, an iron oxide, or zinc oxide, provided that the rate of the inorganic oxide particles is 20 wt % or less. Within this range, the organic-inorganic composite particles can contain the inorganic oxide particles uniformly. Preferable examples of the iron oxide include ferric oxide, α-iron oxyhydroxide, and triiron tetroxide. It is preferable that the inorganic oxide particles have a mean particle diameter substantially equivalent to that of the silica particles. Thus, the mean particle diameter of the inorganic oxide particles is suitably within the range from 5 nm to 1 μm.

To realize a sustainable society, it is preferable to use a silica component produced from a plant-derived raw material. In many countries including Europe and America, there is an increasing demand for organic cosmetic products, in view of harmony with environment and importance of safety. ISO 16128-1 (Guidelines on technical definitions and criteria for natural and organic cosmetic ingredients and products Part1: Definitions for ingredients) defines the raw materials for the organic cosmetic products. Silica sand that is used widely as a source of silica is classified as a mineral component, whereas a plant-derived silica component is classified as a natural component and can raise a natural index of cosmetic products. Thus, such plant-derived silica meets the demand.

A plant-derived silica ingredient is richly contained in gramineous plants, and can be extracted from chaff and ears of rice. It is known that highly pure silica can be obtained by, for example, a calcination method disclosed in JP-A-7-196312 or a pressurized hydrothermal method disclosed in JP-A-2002-265257. The plant-derived silica ingredient obtained in this manner can be dissolved in sodium hydroxide to prepare sodium silicate. Thereafter, silica particles can be prepared according to a method known in the art.

<Biodegradable Plastic>

It is preferable to use, as the biodegradable plastic, biodegradable plastic particles having a mean particle diameter (d) ranging from 1 nm to 1 μm. Organic-inorganic composite particles produced using the biodegradable plastic particles having such a micro mean particle diameter can exhibit a suitable biodegradability. It is particularly preferable that the mean particle diameter of the biodegradable plastic particles be within the range from 0.1 μm to 0.5 μm. Apart from the particles described above, cellulose nanofibers having a thickness ranging from 1 nm to 500 nm and a length of 1 μm or more (measurement based on an electron microscope photograph), and cellulose nanocrystals having a thickness ranging from 10 nm to 50 nm and a length ranging from 100 nm to 500 nm (measurement based on an electron microscope photograph) can also be suitably used as the biodegradable plastic.

A particularly preferable biodegradable plastic is a crystalline cellulose that includes a glucose molecule as a constitutional unit. A further preferable biodegradable plastic is a crystalline cellulose that includes a glucose molecule as a constitutional unit and that has the I-type crystal form. According to the above-described definition in ISO16128-1, an intentionally chemically modified cellulose having no I type crystal form may not be classified as a natural raw material. It is noted that the crystal form of cellulose can be identified by an infrared spectroscopic method, and strong absorption is observed at 3365 to 3370 cm$^{-1}$. Alternatively, the identification also can be performed based on a difference in chemical shift by a solid-state 13C NMR spectroscopic method or a diffraction angle by an X-ray diffraction method. Also, the crystal form may be any one of Iα and Iβ or a mixture thereof.

Although petroleum-derived biodegradable plastics are used industrially in many cases, the biodegradable plastic for the organic-inorganic composite particles of the present invention is not limited to any particular raw materials as long as the biodegradability is achieved. However, to realize a sustainable society, it is preferable to use a biomass plastic that is a renewable organic source, as the biodegradable plastic. Example of the biomass plastic include a chemically-synthesized material (polylactic acid, polycaprolactone, polybutylene succinate, polyethylene succinate, polyvinyl alcohol, polyaspartic acid), a microbially-produced material (pullulan, polyglutamic acid, polyhydroxyalkane acid), and plant- or animal-derived material (starch, cellulose, amylose, chitin, and chitosan). The plant-derived cellulose is particularly suitable in terms of quality, price, marketed amount, and safety.

<Production Method of Organic-Inorganic Composite Particle>

Next, a production method of the organic-inorganic composite particle will be described. First, a mixed liquid containing a dispersion of a silica component and a biodegradable plastic is prepared. To this mixed liquid, a surfactant and a nonaqueous solvent are added to form an emulsified droplet (emulsification step). Then, this emulsified droplet is dehydrated (dehydration step). The obtained dispersion body is separated into solid and liquid to extract an organic-inorganic composite particle as a solid matter (solid-liquid separation step). This solid matter is dried and crushed (drying step).

Hereinafter, each step will be described in detail.

<Emulsification Step>

A mixed liquid containing a dispersion of a silica component and a biodegradable plastic is prepared. Alternatively, the mixed liquid may be prepared by mixing a dispersion liquid of a silica component and a dispersion liquid of a biodegradable plastic. The solid content concentration of this mixed liquid is adjusted to 0.01 to 50%. It is noted that the solvent is preferably water. When the solid content concentration exceeds 50%, the viscosity of the aqueous dispersion body usually increases, and the uniformity of the emulsified droplet is sometimes impaired. When the solid content concentration is less than 0.01%, an advantage is not particularly provided, and economy is poor.

To this mixed liquid, a nonaqueous solvent and a surfactant are added. The nonaqueous solvent necessary for emulsification may be any common hydrocarbon solvent, as long as it is not compatible with water. Also, the surfactant is not particularly limited, as long as it can form a water droplet-in-oil type emulsified droplet. A suitable surfactant is a surfactant having an HLB value ranging from 1 to 10 depending on the polarity of the nonaqueous solvent. The HLB value of the surfactant is particularly preferably in the range of 1 to 5. A combination of surfactants having different HLB values may be used.

Next, this solution is emulsified by an emulsification device. In this manner, an emulsified liquid containing an emulsified droplet of 0.5 to 500 μm is prepared. Examples of the emulsification device include known devices such as a high pressure emulsification device to obtain a finer emulsified droplet, a membrane emulsification device to obtain a more uniform emulsified droplet, and a microchannel emulsification device, as well as common high-speed shear devices.

<Dehydration Step>

Next, the emulsified liquid obtained in the emulsification step is dehydrated. For example, heating under normal pressure or reduced pressure is performed to vaporize water. This hydrates the emulsified droplet to obtain a nonaqueous solvent dispersion body containing an organic-inorganic composite particle having a particle diameter of 0.5 to 25 μm.

Specifically, in a thermal dehydration method under normal pressure, a separable flask equipped with a cooling pipe is heated to perform dehydration while recovering the nonaqueous solvent. Also, in a thermal dehydration method under reduced pressure, heating under reduced pressure is performed using a rotary evaporator or an evaporation can to perform dehydration while recovering the nonaqueous solvent. In the later-described solid-liquid separation step, dehydration is preferably performed until a solid matter can be extracted from the nonaqueous solvent dispersion body. Since the form as a spherical particle cannot be retained in the solid-liquid separation step if dehydration is insufficient, attention is needed.

<Solid-Liquid Separation Step>

In the solid-liquid separation step, a solid content is isolated from the nonaqueous solvent dispersion body obtained in the dehydration step by a known method such as filtration or centrifugation. Accordingly, a cake-like substance of the organic-inorganic composite particle can be obtained.

<Drying Step>

In the drying step, heating under normal pressure or reduced pressure is performed to evaporate the nonaqueous solvent from the cake-like substance obtained in the solid-liquid separation step. Accordingly, there is obtained a dried powder of the organic-inorganic composite particle having an average particle diameter of 0.5 to 25 μm.

It is noted that a freezing step may be included between the emulsification step and the dehydration step. The emulsified droplet obtained in the emulsification step is cooled to −50 to 0° C. to obtain a frozen emulsified product in which water in a droplet is frozen. Subsequently, the frozen emulsified product is dehydrated in the dehydration step. When the freezing temperature is −50° C. to −10° C., a porous organic-inorganic composite particle can be prepared. When −10 to 0° C., the silica component and the biodegradable plastic component in the liquid droplet are expelled to the outer circumference of the droplet with the growth of crystals of ice. Therefore, there can be prepared an organic-inorganic composite particle having a hollow structure which has a cavity inside a shell. In the freezing step, for example, a specific temperature ranging from −10 to 0° C. may be maintained, or the temperature may fluctuate within this range.

Furthermore, the cake-like substance of the organic-inorganic composite particle obtained in the solid-liquid separation step may be washed to reduce the surfactant. When the organic-inorganic composite particle according to the present invention is used for solid formulations such as foundations, a problem is not particularly caused. However, when this organic-inorganic composite particle is used for liquid formulations such as emulsified products, long-term stability is sometimes impaired. Therefore, it is preferable that the residue amount of the surfactant to the organic-inorganic composite particle becomes 500 ppm or less. For reducing the surfactant, washing with an organic solvent may be performed.

<Cosmetic Product>

Cosmetic products produced by blending the organic-inorganic composite particles with various cosmetic ingredients will be described in detail below.

Unlike the known particles consisting of a single inorganic component such as silica particles, the organic-inorganic composite particles of the present invention used in a cosmetic product can provide main texture characteristics required for a texture improver for cosmetic products. Specifically, the particles of the present invention provide not only the rolling effect, the duration of rolling effect, and the uniform spreadability, but also soft texture and moist texture that are unique to plastic beads.

Various cosmetic ingredients are exemplified below. Olive oil, rapeseed oil, and beef tallow as oils and fats. Jojoba oil, carnuba wax, candelilla wax, and beeswax as waxes. Paraffin, squalane, synthetic and vegetable squalane, α-olefin oligomers, microcrystalline wax, pentane, and hexane as hydrocarbons. Stearic acid, myristic acid, oleic acid, and α-hydroxy acid as fatty acids. Isostearyl alcohol, octyldodecanol, lauryl alcohol, ethanol, isopropanol, butyl alcohol, myristyl alcohol, cetanol, stearyl alcohol, and behenyl alcohol as alcohols. Alkyl glyceryl ethers, isopropyl myristate, isopropyl palmitate, ethyl stearate, ethyl oleate, cetyl laurate, and decyl oleate as esters. Ethylene glycol, triethylene glycol, polyethylene glycol, propylene glycol, glycerin, and diglycerin as polyhydric alcohols. Sorbitol, glucose, sucrose, and trehalose as saccharides. Methyl polysiloxane, methyl hydrogen polysiloxane, methyl phenyl silicone oil, various modified silicone oils, and cyclic dimethyl silicon oil as silicone oil. Silicone gel crosslinked by silicone-based and/or other organic compounds. Various nonionic, cationic, and anionic surfactants. Fluorine oil such as perfluoropolyether. Various polymers such as gum arabic, carrageenan, agar, xanthan gum, gelatin, alginic acid, guar gum, albumin, pullulan, carboxyvinyl polymers, cellulose and derivatives thereof, polyacrylic acid amide, sodium polyacrylate, and polyvinyl alcohol. Animal or plant extracts. Amino acid and peptides. Vitamins. UV protectors based on cinnamic acid such as octyl paramethoxycinnamate, salicylic acid, benzoic acid ester, urocanic acid, benzophenone, and the like. Antiseptic and preservative agents. Antioxidants. Modified or unmodified clay minerals. Solvents such as butyl acetate, acetone, and toluene. Various organic pigments and dyes. Water. Flavors. Titanium oxide, zinc oxide, aluminum oxide, aluminum hydroxide, red iron oxide, yellow iron oxide, black iron oxide, cerium oxide, zirconium oxide, silica, mica, talc, sericite, boron nitride, barium sulfate, mica titanium having peal-like gloss, each having various particle diameters, particle diameter distributions, and shapes, and composites thereof. Here, the surface of inorganic compounds such as titanium oxide and zinc oxide may be previously subjected to a silicone treatment, a fluorine treatment, a metal soap treatment, or the like.

Also, resin particles such as methyl polyacrylate, nylon, silicone resin, silicone rubber, polyethylene, polyester, and polyurethane may be contained.

Furthermore, as ingredients having whitening effects, there may be contained arbutin, kojic acid, vitamin C, sodium ascorbate, magnesium ascorbate phosphate, ascorbyl dipalmitate, glucoside ascorbate, other ascorbic acid derivatives, placenta extracts, sulfur, plant extracts such as oil-soluble licorice extracts and mulberry extracts, linolic acid, linoleic acid, lactic acid, and tranexamic acid.

Also, as ingredients having rough skin remedying effects, there may be contained: active ingredients having anti-aging effects such as vitamin C, carotinoid, flavonoid, tannin, caffeic acid derivatives, lignan, saponin, retinoic acid and retinoic acid structural analogs, N-acetylglucosamine, and -hydroxy acid; polyhydric alcohols such as glycerin, propylene glycol, and 1,3-butylene glycol; saccharides such as saccharide isomerate, trehalose, and pullulan; biopolymers such as sodium hyaluronate, collagen, elastin, chitin/chitosan, and sodium chondroitin sulphate; amino acid, betaine, ceramide, sphingolipid, ceramide, cholesterol and derivatives thereof, -aminocaproic acid, glycyrrhizic acid, and various vitamins.

Furthermore, there may be blended cosmetic ingredients described in the Japanese Standards of Quasi-drug Ingredients 2006 (issued by Yakuji Nippo, Limited, Jun. 16, 2006), International Cosmetic Ingredient Dictionary and Handbook (issued by The Cosmetic, Toiletry, and Fragrance Association, Eleventh Edition, 2006), and the like.

Such cosmetics can be manufactured by methods known in the art. The cosmetics are used in various forms such as powders, cakes, pencils, sticks, creams, gels, mousse, liquids, and creams. Specific examples of the cosmetics may include washing cosmetics (such as soaps, cleansing foams, and make-up remover creams), skincare cosmetics (cosmetics for moisture retention and skin roughness prevention, acne, cuticle care, massaging, wrinkle and sag treatments, dullness and shadow treatments, UV care, whitening, and antioxidation care), base makeup cosmetics (powder foundations, liquid foundations, cream foundations, mousse foundations, pressed powders, and makeup bases), point makeup cosmetics (eyeshadows, eyebrow makeup, eyeliners, mascaras, and lipsticks), hair-care cosmetics (cosmetics for hair growth, dandruff prevention, itch prevention, washing, conditioning/hair styling, perming or waving, and hair coloring or bleaching), body-care cosmetics (cosmetics for washing, sunscreening, hand roughness prevention, slimming, blood circulation improvement, itch suppression, deodorization, sweat control, and body hair care, repellents, body powders, and the like), fragrance cosmetics (perfume, eau de parfum, eau de toilette, eau de cologne, shower cologne, solid perfume, body lotion, and bath oil), and oral care products (toothpastes and mouthwashes).

EXAMPLES

Hereinafter, examples of the present invention will be specifically described.

Example 1

Fifty grams of a commercially available silica sol (SS-300 manufactured by JGC Catalysts and Chemicals Ltd., average particle diameter 300 nm, silica concentration 20% by mass) is concentrated by a rotary evaporator to obtain 25 g of a silica sol having a silica concentration of 40% by mass. To this silica sol, a cation resin (SK-1B manufactured by Mitsubishi Kasei Corporation) is added at a stretch such that the pH becomes 2.5. Thereafter, the cation exchange resin is isolated. This enables dealkalization (for example, removal of Na ions) to obtain a slurry a having a silica particle concentration of 39.3% by mass. A slurry b is prepared by adding, to the slurry a, a polymer dispersion liquid in which 10 g of a I-type cellulose particle (Ceolus (registered trademark) RC-N30 manufactured by Asahi Kasei Corporation) and 30 g of pure water are uniformly dispersed.

The obtained slurry b is added to a solution in which 1300 g of heptane (manufactured by Kanto Chemical Co., Ltd.) and 9.75 g of an AO-10V surfactant (manufactured by Kao Corporation) are mixed. The obtained product is emulsified at 10000 rpm for 10 minutes using an emulsification disperser (T.K. ROBOMIX manufactured by PRIMIX Corporation). The resultant emulsified liquid is heated at 60° C. for 16 hours to dehydrate the emulsified droplet. Thereafter, filtration is performed with a quantitative filter paper (No. 2, manufactured by Advantec Toyo Kaisha, Ltd.), using a Buchner funnel (3.2 L, manufactured by Sekiya Chemical Glass Apparatus Co., Ltd.). Thereafter, washing with heptane is repeated for removing the surfactant to obtain a cake-like substance. This cake-like substance is dried at 120° C. for 12 hours. This dried powder was pulverized for 10 seconds by a juicer/mixer device (manufactured by Hitachi, Ltd.) and sifted with a 250 mesh sieve (standard sieve for JIS test) to obtain a powder of an organic-inorganic composite particle. The preparation condition of the organic-inorganic composite particle is illustrated in Table 1 for each example. Also, the physical properties of the powder of the organic-inorganic composite particle were measured in the following method. The results are illustrated in Table 2.

(1) Average Particle Diameter ($d_1$, $d_2$, or $d_4$) of Each Particle

By a laser diffraction method, the particle size distribution of each of the organic-inorganic composite particle, the silica particle, and the biodegradable plastic particle was measured. The median diameter calculated from this particle size distribution was defined as the average particle diameter. In this manner, the average particle diameter $d_1$ of the organic-inorganic composite particle, the average particle diameter $d_2$ of the silica particle, and the average particle diameter $d_4$ of the biodegradable plastic particle were calculated. In the measurement of the particle size distribution by a laser diffraction method, an LA-950v2 laser diffraction/scattering particle diameter distribution measuring device (manufactured by Horiba, Ltd.) was used. However, for the average particle diameter $d_4$ of a fibrous biodegradable plastic particle represented by a cellulose nanofiber, a cellulose nanocrystal, or the like, the average particle diameter in terms of the equivalent sphere was calculated from the specific surface area and the specific gravity of the particle according to the following formula.

"Average particle diameter"=6000/("true density"× "specific surface area")

(2) The Mean Particle Diameter Ratio ($d_3/d_1$)

When the mean particle diameter of the organic-inorganic composite particles was measured using the laser diffraction/scattering particle size distribution analyzer LA-950v2, the dispersion condition of the analyzer was set to "ultrasonic dispersion for 60 minutes". Following the ultrasonic dispersion, a particle size distribution was measured, and a mean particle diameter (d3) represented by the median diameter was determined from the measured particle size distribution. Thus, we obtained the mean particle diameter ratio ($d_3/d_1$) between the mean particle diameters ($d_3$) and ($d_1$) depending on ultrasound dispersion.

(3) Measurement Method of True Density of Organic-Inorganic Composite Particle

About 30 ml of the organic-inorganic composite particles were put in a porcelain crucible (type B-2) and dried at 105° C. for 2 hours. Thereafter, the organic-inorganic composite particles were cooled to room temperature in a desiccator. Next, 15 ml of the sample was taken and the true density thereof was measured using an automatic pycnometer (Ultrapyc1200e, manufactured by Quantachrome Instruments).

(4) A Coefficient of Variation of the Silica Particles

A photograph (SEM photograph) was taken with a magnification of 20,000 to 250,000 using the scanning electron microscope (JSM-7600F, manufactured by JEOL Ltd.). The mean particle diameter of 250 particles in this photograph was measured using an image analyzer (IP-1000, manufactured by Asahi Kasei Corporation). The coefficient of variation (CV value) in relation with the particle size distribution was calculated.

(5) A Sphericity

A photograph projection was obtained by photographing the particles with a magnification of 2,000 to 250,000 using a transmission electron microscope (H-8000, manufactured by Hitachi, Ltd.), and arbitrary 50 particles were selected from the photograph projection. For each of the selected particles, the maximum diameter (DL) and the short diameter (DS) orthogonal to the maximum diameter (DL) were measured, and the ratio (DS/DL) was obtained. The mean value of the ratios was determined as the sphericity.

(6) A Specific Surface Area of the Organic-Inorganic Composite Particles

About 30 ml of the organic-inorganic composite particle powder was put in a porcelain crucible (type B-2) and dried at 105° C. for two hours. Thereafter, the organic-inorganic composite particle powder was cooled to room temperature in a desiccator. Next, 1 g of the sample was taken and the specific surface area (m2/g) thereof was measured by the BET method using a full-automatic surface area measuring device (Multisorb 12, manufactured by Yuasa Ionics Inc.).

The specific surface area per unit volume was obtained by converting the measured specific surface area with the specific gravity (for example, 2.2 g/cm$^3$ when silica is 100%, and 1.5 g/cm$^3$ when cellulose is 100%) calculated from the composition ratio (formulated weight ratio) between the silica and the biodegradable plastic formulated in the organic-inorganic composite particle.

(7) Pore Volume and Pore Diameter of Organic-Inorganic Composite Particle

In a crucible, 10 g of the organic-inorganic composite particle powder was dried at 105° C. for one hour. The powder was then cooled to room temperature in a desiccator. The measurement of the pore size distribution was conducted by a mercury porosimetry method using an automatic porosimeter (PoreMasterPM33GT, manufactured by Quantachrome Instruments). Mercury was injected at a pressure from 1.5 kPa to 231 MPa. The pore size distribution was obtained from the relation between the pressure and the pore diameter. According to this method, mercury was injected into the pores from approximately 7 nm to approximately 1000 μm.

Therefore, both the small-diameter pores existing in the organic-inorganic composite particle and the space between the organic-inorganic composite particles appear in the pore size distribution. The space between the organic-inorganic composite particles has a size of approximately ⅕ to ½ of the mean particle diameter of the organic-inorganic composite particles. Based on the results of measurement of the small-diameter pores excluding this space, the pore volume, the mean were calculated.

Here, the peak separation software (attached to the automatic porosimeter) was used as necessary.

(8) Analyzing a Composition of the Organic-Inorganic Composite Particles

On a platinum plate, 0.2 g of the organic-inorganic composite particle powder was precisely weighted. Then, 10 ml of sulfuric acid and 10 ml of hydrofluoric acid were added thereto and the mixture was heated on the sand bath until the white smoke of sulfuric acid came. After the mixture was cooled, about 50 ml of water was added and the mixture was dissolved by heat. After the mixture was cooled, the mixture was diluted into 200 ml of water, and the resulting mixture was treated as a test solution. With this test solution, the composition of the organic-inorganic composite particles was determined using an inductively coupled plasma emission spectrometer (ICPS-8100, Analysis software ICPS-8000, manufactured by SHIMADZU CORPORATION).

(9) A Contact Angle

Following drying of 1 g of the organic-inorganic composite particles at 105° C., the particles were put into a cell having a diameter of 1 cm and a height of 5 cm, and then pressed with a load of 50 kgf, thereby obtaining a pressed mass of particles. A drop of water was put onto the pressed mass, and a contact angle with water was measured.

(10) The Modulus of Elasticity

From the organic-inorganic composite particle powder, one particle which was within the range of ±0.5 μm with respect to the mean particle diameter was taken as a specimen. A modulus of elasticity in compression of the specimen was measured using a micro compression tester (MCTM-200, manufactured by SHIMADZU CORPORATION), while a load was applied to the specimen at a constant load rate.

Example 2

Instead of the I-type cellulose particle in the polymer dispersion liquid used in Example 1, a BiNFi-s WMa-10002 manufactured by Sugino Machine Limited was used. Otherwise, an organic-inorganic composite particle was prepared in the same manner as in Example 1, and the physical properties were measured in the same manner as in Example 1.

Example 3

Instead of the I-type cellulose particle in the polymer dispersion liquid used in Example 1, a RHEOCRYSTA C-2SP manufactured by DKS Co. Ltd. was used. Otherwise, an organic-inorganic composite particle was prepared in the same manner as in Example 1, and the physical properties were measured in the same manner as in Example 1.

Example 4

The mixed amount of the I-type cellulose particle (Ceolus (registered trademark) RC-N30 manufactured by Asahi Kasei Corporation) in the polymer dispersion liquid was changed to 4.3 g. Otherwise, an organic-inorganic composite particle was prepared in the same manner as in Example 1, and the physical properties were measured in the same manner as in Example 1.

Example 51

The mixed amount of the I-type cellulose particle (Ceolus (registered trademark) RC-N30 manufactured by Asahi Kasei Corporation) in the polymer dispersion liquid was changed to 23.3 g. Otherwise, an organic-inorganic composite particle was prepared in the same manner as in Example 1, and the physical properties were measured in the same manner as in Example 1.

Example 6

The emulsified liquid was left to stand in a constant temperature bath at −5° C. for 16 hours to freeze the emulsified droplet. Furthermore, the emulsified liquid was left to stand at normal temperature and thereafter filtrated through a quantitative filter paper (No. 2, manufactured by Advantec Toyo Kaisha, Ltd.) with a Buchner funnel (3.2 L, manufactured by Sekiya Chemical Glass Apparatus Co., Ltd.). Otherwise, an organic-inorganic composite particle was prepared in the same manner as in Example 1, and the physical properties were measured in the same manner as in Example 1.

Example 71

The emulsified liquid was left to stand in a constant temperature bath at −25° C. for 16 hours to freeze the emulsified droplet. Otherwise, an organic-inorganic composite particle was prepared in the same manner as in Example 6, and the physical properties were measured in the same manner as in Example 1.

Example 8

As the silica sol, 62.5 g of a commercially available product (SS-160 manufactured by JGC Catalysts and Chemicals Ltd., average particle diameter 160 nm, solid content concentration 16% by mass) was used. This commercially available product was concentrated by an evaporator to obtain a silica sol having a silica concentration of 40% by weight. Otherwise, an organic-inorganic composite particle was prepared in the same manner as in Example 1, and the physical properties were measured in the same manner as in Example 1.

Example 9

As the silica sol, 50 g of a commercially available product (SI-550 manufactured by JGC Catalysts and Chemicals Ltd., average particle diameter 5 nm, solid content concentration 20% by mass) was used. The concentration by an evaporator was not performed. Otherwise, an organic-inorganic composite particle was prepared in the same manner as in Example 1, and the physical properties were measured in the same manner as in Example 1.

Example 10

As the slurry a, 200 g of a silicic acid liquid (solid content concentration 5%) was used. A slurry b was prepared by adding, to this silicic acid liquid, a polymer dispersion liquid in which 10 g of a I-type cellulose particle (Ceolus (registered trademark) RC-N30 manufactured by Asahi Kasei Corporation) and 30 g of pure water were uniformly dispersed. Thereafter, an organic-inorganic composite particle was prepared in the same manner as in Example 6, and the physical properties were measured in the same manner as in Example 1.

Example 11

Emulsification was performed at 5000 rpm for 10 minutes using an emulsification disperser (T.K. ROBOMIX manufactured by PRIMIX Corporation). Otherwise, an organic-inorganic composite particle was prepared in the same manner as in Example 1, and the physical properties were measured in the same manner as in Example 1.

Comparative Example 1

The mixed amount of the cellulose particle (Ceolus (registered trademark) RC-N30 manufactured by Asahi Kasei Corporation) in the polymer dispersion liquid was changed to 1.1 g. Otherwise, an organic-inorganic composite particle was prepared in the same manner as in Example 1, and the physical properties were measured in the same manner as in Example 1.

Comparative Example 2

The emulsified liquid was heated at 95° C. for 4 hours. Otherwise, an organic-inorganic composite particle was prepared in the same manner as in Example 1, and the physical properties were measured in the same manner as in Example 1. Since heating was performed rapidly at high temperature, the emulsified droplet broke before dehydration. Therefore, a particle having a high sphericity could not be obtained.

Comparative Example 3

Emulsification was performed at 500 rpm for 10 minutes using an emulsification disperser (T.K. ROBOMIX manufactured by PRIMIX Corporation). Otherwise, an organic-inorganic composite particle was prepared in the same manner as in Example 1, and the physical properties were measured in the same manner as in Example 1.

TABLE 1

| | Slurry a — Silica component | | | | Polymer dispersion liquid — Biodegradable plastic | | Slurry b |
|---|---|---|---|---|---|---|---|
| | Type | Average particle diameter ($d_2$) (nm) | Coefficient of variance (%) | Sphericity | Type | Average particle diameter ($d_4$) (nm) | Solid content weight mixed ratio (VII) |
| Example 1 | A | 300 | 8.0 | 0.93 | I-type cellulose particle (1) | 300 | 50/50 |
| Example 2 | A | 300 | 8.0 | 0.93 | I-type cellulose particle (2) | 100 | 50/50 |
| Example 3 | A | 300 | 8.0 | 0.93 | I-type cellulose particle (3) | 11 | 50/50 |
| Example 4 | A | 300 | 8.0 | 0.93 | I-type cellulose particle (1) | 300 | 70/30 |
| Example 5 | A | 300 | 8.0 | 0.93 | I-type cellulose particle (1) | 300 | 30/70 |
| Example 6 | A | 300 | 8.0 | 0.93 | I-type cellulose particle (1) | 300 | 50/50 |
| Example 7 | A | 300 | 8.0 | 0.93 | I-type cellulose particle (1) | 300 | 50/50 |
| Example 8 | B | 160 | 9.0 | 0.89 | I-type cellulose particle (1) | 300 | 50/50 |
| Example 9 | C | 5 | 9.0 | 0.94 | I-type cellulose particle (1) | 300 | 2/98 |
| Example 10 | D | — | — | — | I-type cellulose particle (1) | 300 | 50/50 |
| Example 11 | A | 300 | 8.0 | 0.93 | I-type cellulose particle (1) | 300 | 50/50 |
| Comparative Example 1 | A | 300 | 8.0 | 0.93 | I-type cellulose particle (1) | 300 | 90/10 |
| Comparative Example 2 | A | 300 | 8.0 | 0.93 | I-type cellulose particle (1) | 300 | 50/50 |
| Comparative Example 3 | A | 300 | 8.0 | 0.93 | I-type cellulose particle (1) | 300 | 50/50 |

| | Emulsification condition | | dehydration condition | |
|---|---|---|---|---|
| | Emulsification dispersion rate (rpm) | Emulsification time (min.) | Condition | Dehydration time (min.) |
| Example 1 | 10000 | 10 | Heating (60° C.) | 960 |
| Example 2 | 10000 | 10 | Heating (60° C.) | 960 |
| Example 3 | 10000 | 10 | Heating (60° C.) | 960 |
| Example 4 | 10000 | 10 | Heating (60° C.) | 960 |
| Example 5 | 10000 | 10 | Heating (60° C.) | 960 |
| Example 6 | 10000 | 10 | Freezing (−5° C.) | 960 |
| Example 7 | 10000 | 10 | Freezing (−25° C.) | 960 |
| Example 8 | 10000 | 10 | Heating (60° C.) | 960 |
| Example 9 | 10000 | 10 | Heading (60° C.) | 960 |
| Example 10 | 10000 | 10 | Freezing (−5° C.) | 960 |
| Example 11 | 5000 | 10 | Heating (60° C.) | 960 |
| Comparative Example 1 | 10000 | 10 | Heating (60° C.) | 960 |
| Comparative Example 2 | 10000 | 10 | Heating (95° C.) | 240 |
| Comparative Example 3 | 500 | 10 | Heating (60° C.) | 960 |

Silica component type A: SS-300 manufactured by JGC Catalysts and Chemicals Ltd. (average particle diameter 300 nm)
Silica component type B: SS-160 menufactured by JGC Catalysts and Chemicals Ltd. (average particle diameter 160 nm)
Silica component type C: Cataloid Si-550 manufactured by JGC Catalysts and Chemicals Ltd. (average particle diameter 5 nm)
Silica component type D: silicic acid liquid (solid content concentration 5%)
I-type cellulose particle (1): Ceolus (registered trademark) RC-N30 manufactured by Asahi Kasal Corporation (crystalline cellulose)
I-type cellulose particle (2): BINFI-e WMa-10002 manufactured by Sugino Machine Limited (crystalline cellulose)
I-type cellulose particle (3): RHEOCRYSTA C-2SP manufactured by DKS Co. Ltd. (crystalline cellulose)

TABLE 2

| | Organic-inorganic composite particle | | | | | | |
|---|---|---|---|---|---|---|---|
| | Average particle diameter $d_1$ [mm] | True density [g/cm$^3$] | Sphericity | Specific surface area [m$^2$/cm$^3$] | Pore volume [mL/g] | Contact angle to water | Elastic modulus [Gpa] |
| Example 1 | 4.8 | 1.85 | 0.84 | 20 | 0.25 | 48° | 15 |
| Example 2 | 4.2 | 1.85 | 0.84 | 100 | 0.22 | 55° | 14 |
| Example 3 | 3.8 | 1.85 | 0.84 | 273 | 0.20 | 62° | 11 |
| Example 4 | 4.9 | 1.99 | 0.90 | 20 | 0.25 | 49° | 10 |
| Example 5 | 4.5 | 1.71 | 0.82 | 20 | 0.25 | 50° | 16 |
| Example 6 | 8.2 | 1.85 | 0.85 | 20 | 0.62 | 48° | 15 |
| Example 7 | 7.9 | 1.85 | 0.84 | 20 | 0.64 | 48° | 15 |
| Example 8 | 4.8 | 1.85 | 0.82 | 29 | 0.24 | 47° | 16 |
| Example 9 | 3.5 | 1.51 | 0.81 | 44 | 0.25 | 53° | 18 |
| Example 10 | 6.6 | 1.30 | 0.85 | 3 | 0.01 | 55° | 5 |
| Example 11 | 12.0 | 1.85 | 0.81 | 20 | 0.25 | 48° | 20 |
| Comparative Example 1 | 4.4 | 2.13 | 0.86 | 20 | 0.26 | 48° | 1 |
| Comparative Example 2 | 3.2 | 1.85 | 0.72 | 20 | 0.27 | 48° | 13 |
| Comparative Example 3 | 38.0 | 1.85 | 0.80 | 20 | 0.25 | 48° | 18 |

| | Organic-inorganic composite particle | | | |
|---|---|---|---|---|
| | $d_3/d_1$ | Interior structure | Silica component [wt %] | Biodegradable plastic component [wt %] |
| Example 1 | 0.01 | Porous solid | 50 | 50 |
| Example 2 | 0.01 | Porous solid | 50 | 50 |
| Example 3 | 0.01 | Porous solid | 50 | 50 |
| Example 4 | 0.03 | Porous solid | 70 | 30 |
| Example 5 | 0.01 | Porous solid | 30 | 70 |
| Example 6 | 0.02 | Porous hollow | 50 | 50 |
| Example 7 | 0.01 | Porous solid | 50 | 50 |
| Example 8 | 0.03 | Porous solid | 50 | 50 |
| Example 9 | 0.04 | Porous solid | 2 | 98 |
| Example 10 | 0.01 | Nonporous hollow | 50 | 50 |
| Example 11 | 0.04 | Porous solid | 50 | 50 |
| Comparative Example 1 | 0.06 | Porous solid | 90 | 10 |
| Comparative Example 2 | 0.06 | Porous solid | 50 | 50 |
| Comparative Example 3 | 0.04 | Porous solid | 50 | 50 |

[Texture Properties of Power of Organic-Inorganic Composite Particle]

Next, the powders obtained in Examples and Comparative Examples were evaluated for their texture properties. Each of the powders was subjected to a sensory test by 20 expert panelists. The panelists are interviewed regarding seven evaluation items: loose sense, moisture sense, rolling sense, uniform spreadability, adherence to skin, persistence of rolling sense, and soft sense. Evaluation is performed in accordance with the following evaluation point criteria (a). Based on the total of the evaluation points by the panelists, the texture of the organic-inorganic composite particle was evaluated in accordance with the following evaluation criteria (b). The results are illustrated in Table 3. As a result, it was found that the powders of Examples are significantly excellent as a texture improver for cosmetic products, but the powders of Comparative Examples are not suitable as a texture improver.

Evaluation Point Criteria (a)
  5 points: very superior
  4 points: superior
  3 points: average
  2 points: inferior
  1 point: very inferior Evaluation Criteria (b)
  Excellent: not less than 80 points in total
  Good: not less than 60 and less than 80 points in total
  Fair: not less than 40 and less than 60 points in total
  Poor: not less than 20 and less than 40 points in total
  Bad: less than 20 points in total

TABLE 3

| Evaluation sample | Loose sense | Moisture sense | Rolling sense | Uniform spread | Adherence to skin | Persistence of rolling sense | Soft sense |
|---|---|---|---|---|---|---|---|
| Example 1 | Good | Good | Good | Good | Good | Good | Good |
| Example 2 | Good | Good | Good | Good | Good | Good | Good |
| Example 3 | Fair | Excellent | Fair | Good | Excellent | Fair | Excellent |
| Example 4 | Excellent | Fair | Excellent | Good | Fair | Excellent | Fair |

TABLE 3-continued

| Evaluation sample | Loose sense | Moisture sense | Rolling sense | Uniform spread | Adherence to skin | Persistence of rolling sense | Soft sense |
|---|---|---|---|---|---|---|---|
| Example 5 | Fair | Excellent | Fair | Fair | Excellent | Poor | Excellent |
| Example 6 | Excellent | Good | Good | Fair | Poor | Excellent | Good |
| Example 7 | Excellent | Fair | Good | Fair | Fair | Good | Good |
| Example 8 | Fair | Good | Fair | Fair | Good | Good | Good |
| Example 9 | Poor | Excellent | Poor | Poor | Good | Poor | Good |
| Example 10 | Good | Excellent | Good | Good | Excellent | Excellent | Excellent |
| Example 11 | Excellent | Poor | Excellent | Good | Poor | Excellent | Fair |
| Comparative Example 1 | Excellent | Bad | Good | Good | Poor | Good | Bad |
| Comparative Example 2 | Bad | Good | Bad | Bad | Fair | Bad | Bad |
| Comparative Example 3 | Excellent | Bad | Excellent | Good | Poor | Good | Bad |

[Feeling of Using Powder Foundation]

Using the organic-inorganic composite particles powder, powder foundation was formed at the blend ratios (% by weight) illustrated in Table 4: The powder of particles of Example 1 (ingredients (1)) and other ingredients (2) to (9) were poured into a mixer. The mixture was stirred to be uniformly mixed. Next, cosmetic ingredients (10) to (12) were poured into this mixer. The mixture was stirred to be further uniformly mixed. The obtained cake-like substance was pulverized. Thereafter, about 12 g of the pulverized substance was taken, and placed in a 46 mm 54 mm 4 mm square metal dish for press molding. Twenty specialized panelists conducted a sensory test on this obtained powder foundation. In the test, the following six evaluation items were studied by hearing: uniform spreadability, a moist feel, and smoothness during application onto the skin, and uniformity of a cosmetic film, a moist feel, and softness after application to the skin. The results are evaluated based on the above-described evaluation point criteria (a). Also, evaluation points scored by the panelists were totaled, and the use feels of the foundation was evaluated based on the above-described evaluation criteria (b). The results are illustrated in Table 5. Here, cosmetic products A to C according to Examples 1 to 3 were evaluated as representative examples. It was found that the feeling of using the cosmetic products A to C based on Examples is very superior both during and after the application. However, it was found that the feeling of using cosmetic products a to c of Comparative Examples 1 to 3 is not good.

TABLE 4

| | Cosmetic components constituting powder foundation | Formulation amount/wt % |
|---|---|---|
| (1) | Powder of Examples 1 to 3 and Comparative Examples 1 to 3 | 10.0 |
| (2) | Sericite (silicon-treated) | 40.0 |
| (3) | Talc (silicon-treated) | 29.0 |
| (4) | Mica (silicon-treated) | 5.0 |
| (5) | Titanium oxide (silicon-treated) | 7.0 |
| (6) | Yellow iron oxide (silicon-treated) | 1.2 |
| (7) | Red iron oxide (silicon-treated) | 0.4 |
| (8) | Black iron oxide (silicon-treated) | 0.2 |
| (9) | Methylparaben | 0.2 |
| (10) | Dimethicone | 4.0 |
| (11) | Liquid paraffin | 2.0 |
| (12) | Glyceryl tri-2-ethylhexanoate | 1.0 |

TABLE 5

| | During application | | | After application | | |
|---|---|---|---|---|---|---|
| Evaluation sample | Uniform spread | Moisture sense | Smoothness | Uniformity of film | Moisture sense | Softness |
| Example 1 (Cosmetic A) | Excellent | Fair | Good | Excellent | Good | Excellent |
| Example 2 (Cosmetic B) | Good | Good | Excellent | Excellent | Good | Excellent |
| Example 3 (Cosmetic C) | Good | Excellent | Excellent | Fair | Excellent | Excellent |
| Comparative Example 1 (Cosmetic a) | Excellent | Bad | Bad | Excellent | Bad | Bad |
| Comparative Example 2 (Cosmetic b) | Bad | Poor | Bad | Bad | Good | Bad |
| Comparative Example 3 (Cosmetic c) | Excellent | Bad | Bad | Good | Bad | Bad |

What is claimed is:

1. A spherical organic-inorganic composite particle comprising:
    1.0 to 83.0% by weight of a silica component; and
    17.0 to 99.0% by weight of biodegradable plastic particles, wherein
    an average particle diameter $d_1$ of the spherical organic-inorganic composite particle is 0.5 to 25 μm,
    a true density of the spherical organic-inorganic composite particle is 1.03 to 2.00 g/cm³, a sphericity of the spherical organic-inorganic composite particle is 0.80 or more, and the biodegradable plastic particles are bound each other by the silica component so as to form the spherical organic-inorganic composite particle.

2. The organic-inorganic composite particle according to claim 1, wherein a contact angle of the spherical organic-inorganic composite particle to water is 90° or less.

3. The organic-inorganic composite particle according to claim 1, wherein a modulus of elasticity of the spherical organic-inorganic composite particle is 2 to 30 GPa.

4. The organic-inorganic composite particle according to claim 1, wherein when a dispersion liquid of the organic-inorganic composite particle is dispersed by an ultrasonic disperser for 60 minutes, a ratio ($d_3/d_1$) between an average particle diameter $d_3$ of the spherical organic-inorganic composite particle after dispersion and the average particle diameter $d_1$ before dispersion is in a range of 0.95 to 1.05.

5. The organic-inorganic composite particle according to claim 1, wherein the silica component contains a silica particle having an average particle diameter $d_2$ ranging from 5 nm to 1 µm.

6. The organic-inorganic composite particle according to claim 1, wherein an average particle diameter $d_4$ of the biodegradable plastic particles is 1 nm to 1 µm.

7. The organic-inorganic composite particle according to claim 1, wherein the biodegradable plastic particles are crystalline cellulose particles having a glucose molecule as a constituent unit.

8. The organic-inorganic composite particle according to claim 1, wherein the organic-inorganic composite particle is a hollow particle having a cavity inside a shell.

9. A cosmetic product including the organic-inorganic composite particle according to claim 1.

10. The organic-inorganic composite particle according to claim 1, wherein the organic-inorganic composite is made by:

adding a surfactant and a nonaqueous solvent to a dispersion liquid of the silica component and the biodegradable plastic particles thereby to prepare an emulsified liquid containing an emulsified droplet;

dehydrating the emulsified droplet to prepare a nonaqueous solvent dispersion body; and separating a solid matter from the nonaqueous solvent dispersion body thereby to obtain the organic-inorganic composite particle.

* * * * *

UNITED STATES PATENT AND TRADEMARK OFFICE
CERTIFICATE OF CORRECTION

PATENT NO. : 11,701,307 B2
APPLICATION NO. : 16/979341
DATED : July 18, 2023
INVENTOR(S) : Satoshi Watanabe et al.

It is certified that error appears in the above-identified patent and that said Letters Patent is hereby corrected as shown below:

In the Specification

Column 5, Line 9, "60 $m^2$/cm" should be --60 $m^2/cm^3$--.

Signed and Sealed this
Twenty-sixth Day of March, 2024

Katherine Kelly Vidal
*Director of the United States Patent and Trademark Office*